United States Patent [19]

Shaw et al.

[11] Patent Number: 5,244,632

[45] Date of Patent: Sep. 14, 1993

[54] APPARATUS FOR SHUTTLING A TEST ELEMENT FROM A DISCHARGE PATH TO A WASH STATION

[75] Inventors: James D. Shaw, Hilton; Martin F. Muszak, Rochester, both of N.Y.

[73] Assignee: Eastman Kodak Company, Rochester, N.Y.

[21] Appl. No.: 951,615

[22] Filed: Sep. 28, 1992

Related U.S. Application Data

[62] Division of Ser. No. 615,530, Nov. 19, 1990, Pat. No. 5,174,960.

[51] Int. Cl.⁵ .............................................. G01N 35/04
[52] U.S. Cl. .................................... 422/63; 422/64; 436/46; 436/48
[58] Field of Search .................... 422/63–65, 422/67; 436/43, 46, 48

[56] References Cited

U.S. PATENT DOCUMENTS

| | | | |
|---|---|---|---|
| 4,584,275 | 4/1986 | Okano et al. | 422/63 |
| 4,855,109 | 8/1989 | Muraishi et al. | 422/63 |
| 4,857,471 | 8/1989 | Salzman et al. | 422/65 |

Primary Examiner—James C. Housel
Assistant Examiner—Jan M. Ludlow
Attorney, Agent, or Firm—Dana M. Schmidt

[57] ABSTRACT

There are disclosed a shuttle apparatus and method for catching a test element ejected from an incubator, for carrying it to a station outside the incubator, e.g., a wash station, and for returning it to a loading station. Preferably, the apparatus comprises a simplified catcher plate and means for moving the plate in an arcuate path around a portion of the circumference of the incubator. The plate cooperates with stop means disposed above said arcuate path, to capture a washed element upon reloading, so that the washed element can be reloaded by returning it to the original path used to load elements into the incubator in the first instance.

7 Claims, 7 Drawing Sheets

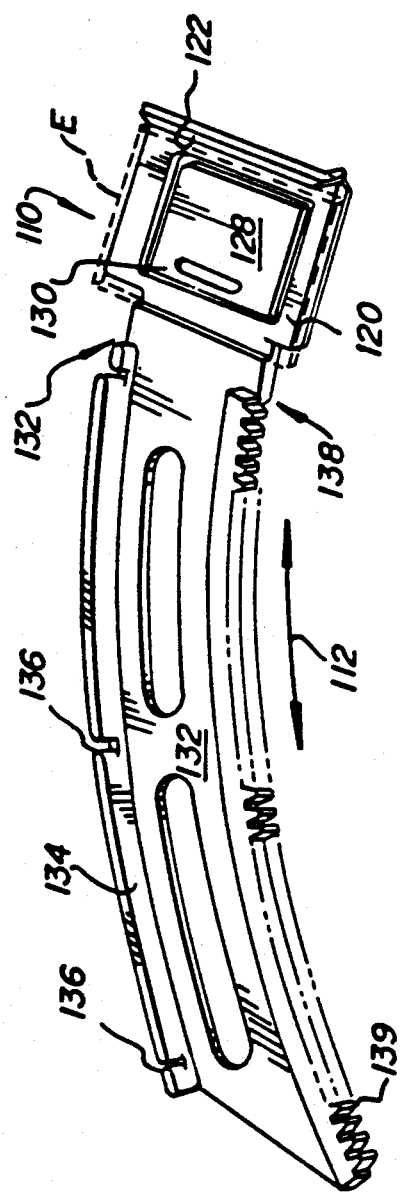
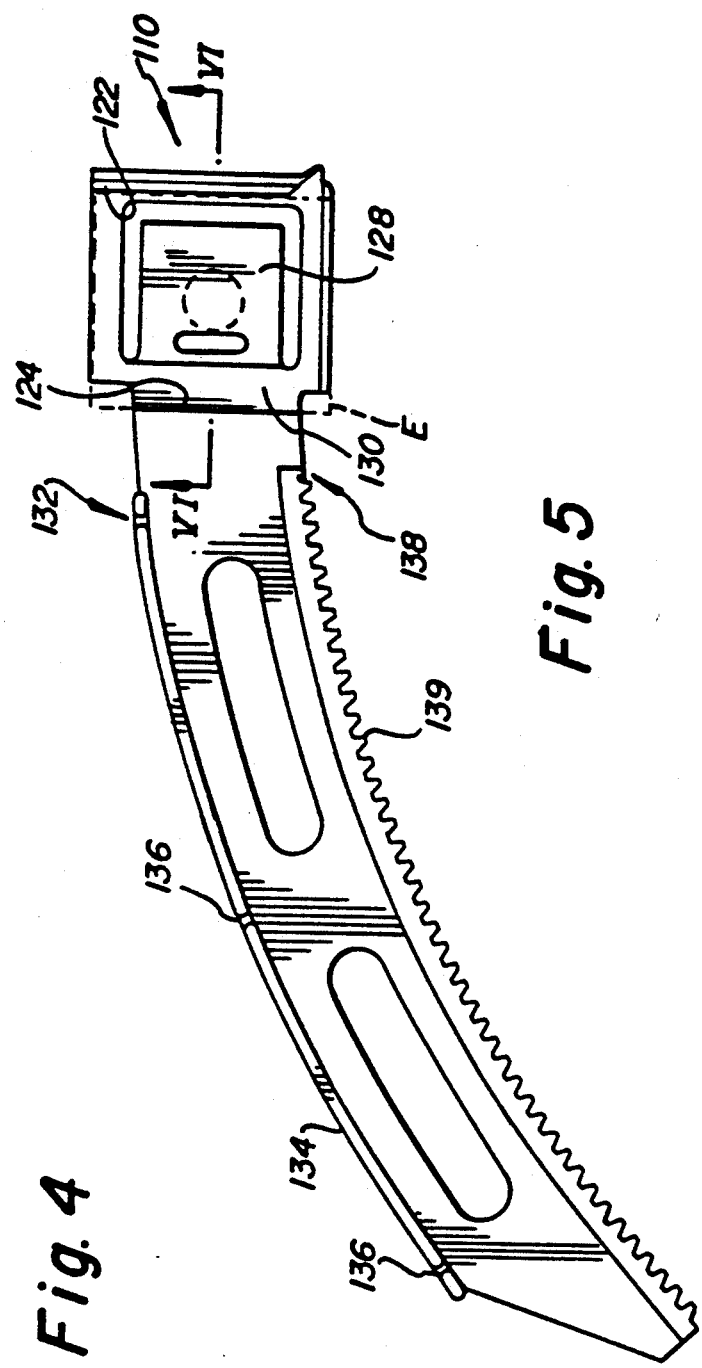

APPARATUS FOR SHUTTLING A TEST ELEMENT FROM A DISCHARGE PATH TO A WASH STATION

This is a division of application Ser. No. 615,530, filed Nov. 19, 1990 now U.S. Pat. No. 5,179,960.

FIELD OF THE INVENTION

The invention relates to an analyzer for ascertaining analyte concentrations in body liquids dispensed onto test elements, particularly such analyzers that need a wash station to allow immunoassays to be conducted.

BACKGROUND OF THE INVENTION

Analyzer mechanisms have been provided for receiving slide test elements from incubators, to carry them on to additional stations, e.g., a wash station. Such a mechanism is described in U.S. Pat. No. 4,857,471. Although this mechanism functions admirably, it uses a platform that lowers into the "dump" path of the ejected slide element to catch the slide element, FIG. 2. The platform cannot move on to the wash station but provides a stationary support. As a result, a claw must then be used to transfer the slide element from this stationary support to a movable train 104. Thus, the noted mechanism does have the disadvantage of requiring a transfer claw and means other than the catching surface to move the slide element to the wash station. Furthermore, the train that is used for the wash step transfer is of substantial size and complexity.

Thus, prior to this invention, there has been a need for an improved transfer mechanism off-line of the incubator, to allow a slide element to be removed from the incubator, washed and reinserted, using simpler and less expensive parts.

SUMMARY OF THE INVENTION

We have constructed a shuttle mechanism and method that solve the aforesaid problems, with a catcher plate that provides the needed movement of a "caught" test element ejected from an incubator, to a wash station and back into a loading station for reinsertion into the incubator. Further, the catcher plate is constructed to provide other important features, all in one simplified piece.

More specifically, in accord with one aspect of the invention, there is provided an analyzer having processing stations including an incubator and a wash station outside of said incubator, means for ejecting a test element from one of the processing stations, and means defining a discharge path to carry the ejected element out of the analyzer. The analyzer is improved in that it further includes a catcher plate for catching test elements ejected from the one processing station by the ejecting means, and means for moving the plate into a position in the discharge path to intercept an ejected element moving along the path, the moving means including means defining a track constructed to move the catcher plate and an intercepted test element from the path to the wash station.

In accord with another aspect of the invention, there is provided an analyzer comprising processing stations including an incubator, means for injecting a test element bearing a sample liquid along a first path into one of the processing stations, means for ejecting a test element from the one station, and discharge means defining a second path for carrying an ejected test element away from the one station. The analyzer is improved in that it further includes a stop mechanism between the first path and the second path, the mechanism including a) a shoulder adjacent the first path to prevent a test element on the first path from moving off the first path towards the second path, and b) a camming surface under and adjacent to the stop shoulder, the camming surface being shaped to cause the stop mechanism to ride up over a test element moved from the vicinity of the second path to the first path, so that a test element can be moved only from the second path to the first path, and not from the first path to the second path.

In accord with yet another aspect of the invention, there is provided a test element support for use in an analyzer that analyzes analytes of a body liquid contained in a test element, the support comprising a plate having a frame, a central portion within and flexibly secured to the frame, and raised shoulders on opposite edges of the frame dimensioned to retain a test element between the shoulders to prevent a held element from being displaced off the support, the central portion being cantilevered from the frame at only one side thereof, so as to be capable of flexing in and out of the plane of the frame.

In accord with still another aspect of the invention, there is provided a method of washing an incubated test element and comprising the steps of loading a test element at a first station into an incubator, ejecting at a second station a loaded test element from the incubator, catching the ejected test element, shuttling the caught element to a wash station, washing the shuttled test element at the wash station, and returning the washed element to the incubator. The method is improved in that the returning step comprises moving the washed element back to the first station, and reloading it into the incubator.

Accordingly, it is an advantageous feature of this invention that the same means that catches a test element ejected from the incubator, is used to transport such test element to a wash station.

It is a related advantageous feature of the invention that the means for transporting a test element from its ejected location to an additional station, is simplified.

It is another advantageous feature of the invention that a removed and washed test element is returned to the original loading mechanism, for reloading into the incubator, to avoid the use of a separate loader.

Other advantageous features will become apparent upon reference to the following Description of the Preferred Embodiments, when read in light of the attached drawings.

BRIEF DESCRIPTION OF THE DRAWINGS

FIG. 4 is a perspective view of the catcher plate that reciprocates within the shuttle apparatus of FIG. 2;

FIG. 5 is a plan view of the catcher plate of FIG. 4, showing in phantom a test element E carried by it;

DESCRIPTION OF THE PREFERRED EMBODIMENTS

The invention is hereinafter described in connection with the preferred embodiments, in which the transfer mechanism that catches and transfers slide-like test elements is disposed outside of an incubator particularly positioned in an analyzer, to transfer the test element to a wash station and back to the incubator, and in which the test elements are of a type similar to those obtained from Eastman Kodak Company under the trademark "Ektachem" slides, or from Fuji Photo under the tradename "Drychem". In addition, such a transfer mechanism is useful adjacent any processing station of an analyzer, whether or not it is the incubator and regardless of the position of that station, to take the slide-like test element to any other processing station and back to the first processing station from which the test element is received. Still further, such a transfer mechanism is useful regardless of the construction of the test element, although generally planar elements are preferred since the transfer mechanism is shaped preferably to handle such planar elements.

Figure 1:
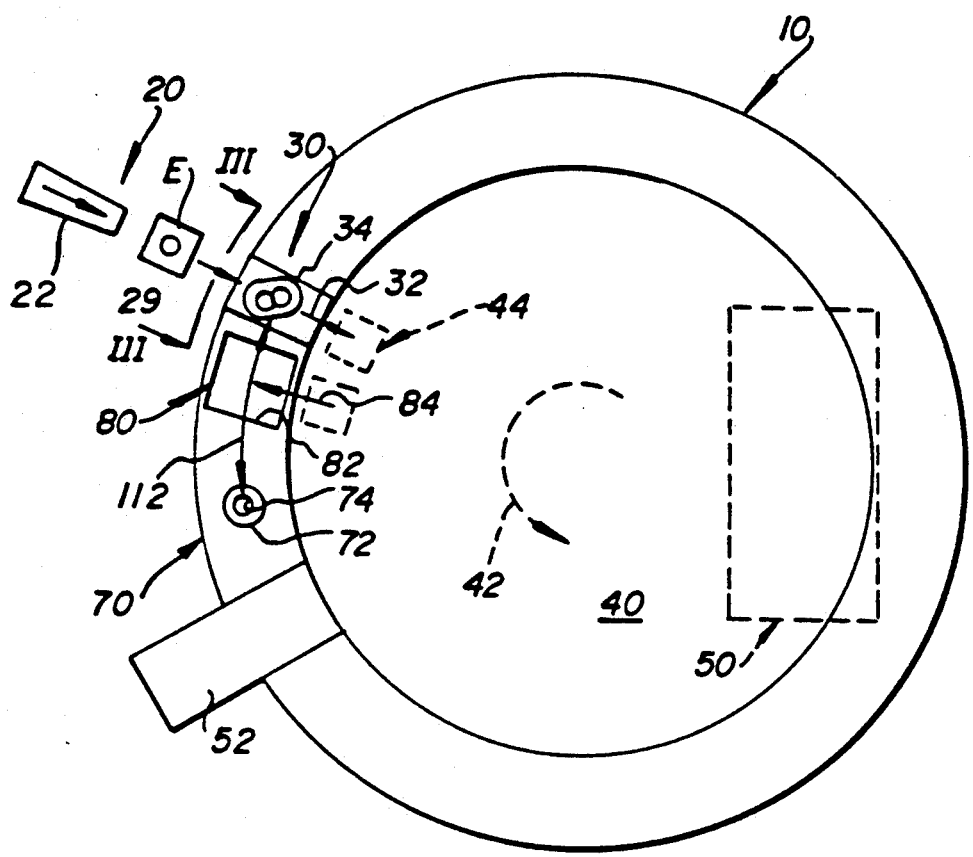
FIG. 1 is a partially schematic, plan view of an analyzer constructed in accordance with the invention.

An analyzer 10 in which this shuttle invention is useful comprises, FIG. 1, preferably a station 20 for loading a slide-like test element E into a sample dispensing station 30, and for loading such an element, along path 32, now bearing patient sample, into an incubator 40. Preferably, loading station 20 includes a pusher blade 22 that pushes an element E along path 29 so as to be injected into station 30. The loading station includes tip locator 34, FIG. 2, with two apertures 36,37 as is conventional for patient sample metering, and an aperture 38 for reference liquid metering, as is also conventional. Also preferably, the incubator is the rotating type, arrow 42 and includes a reflectometer 50, FIG. 1, for scanning colorimetric test elements while they are held at a plurality of stations 44, etc., FIG. 2, as defined by a rotor 46. Such an analyzer includes an electrometer 52, FIG. 1, for reading potentiometric test elements after they are removed from the incubator by, e.g., a pusher blade 48, FIG. 2. A wide variety of incubators is useful for this purpose, for example, that shown in, e.g., U.S. Pat. No. 4,935,374.

Similar to the construction of the analyzer in U.S. Pat. No. 4,857,471, a wash station 70 is disposed outside of incubator 40, displaced circumferentially from station 30. The wash station comprises a boss 72 and aperture 74 that serve to hold a dispensing tip in proper orientation with respect to a test element to be washed. In between stations 30 and 70 is an eject station 80, including a discharge path defined by aperture 82, FIG. 1, into which a test element is ejected, arrow 84, when its readings are completed. Shuttle apparatus is then provided to allow test elements to be intercepted at station 80, taken to wash station 70, and reinserted into the incubator, as in the '471 patent. In accord with one aspect of the invention, it is the improvement of this apparatus to which the invention is addressed.

Figure 2:
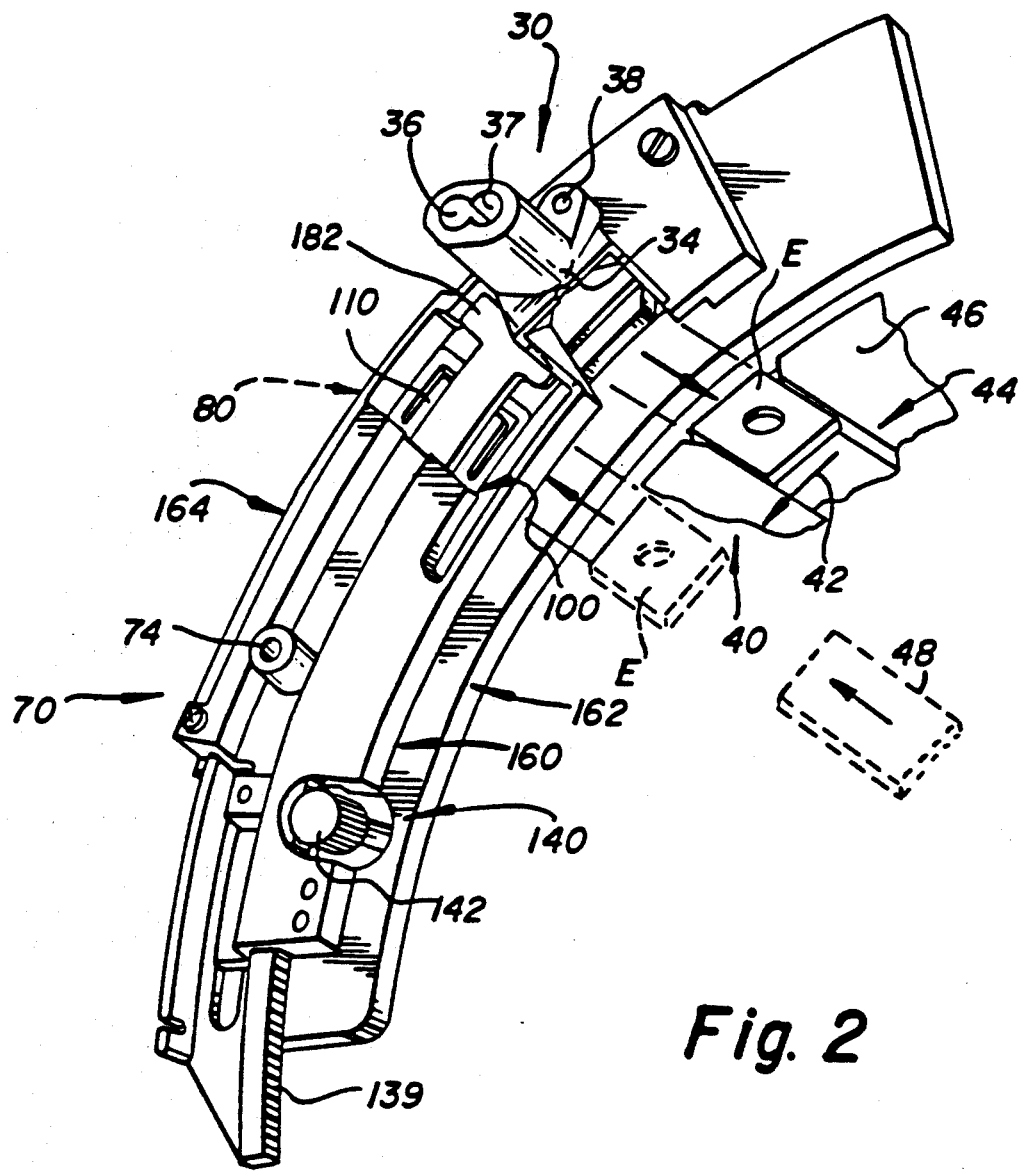
FIG. 2 is a fragmentary perspective view showing especially the shuttle apparatus of the invention outside the incubator.

More specifically, the shuttle apparatus 100, FIG. 2, comprises a catcher plate 110, means 160 for supporting plate 110 for movement along a path 112, FIG. 1 that is preferably curvilinear, and means 140, FIG. 2, for driving plate 110 along path 112, FIG. 1. Importantly, path 112 is constructed to extend back to station 30 to intersect path 32, so that a test element washed at station 70 can be reinserted into the loading path 32.

Figure 6:
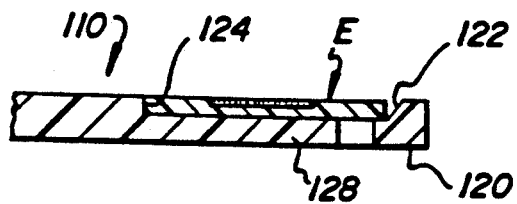
FIG. 6 is a fragmentary, partially schematic (for element E) section view taken generally along the line VI—VI of FIG. 5.

Referring now to FIGS. 4-6, catcher plate 110 comprises a frame 120 shaped to hold a test element E, shown in phantom. Accordingly, frame 120 is generally rectangular, and is provided with two opposed shoulders 122,124 shaped and positioned, FIG. 6, to restrain element E from moving off plate 110 as the latter moves on path 112, FIG. 4. Shoulder 122 is the leading shoulder and is preferably beveled, to allow shoulder 122 to cam under element E when the latter is returned to and retained at path 32, FIG. 1, as described hereinafter.

A central support member 128 is flexibly connected to frame 120, FIG. 4, to do the principal carrying of element E. The flexibility is achieved by reason of the cantilever connection of support member 128 at one side 130 of frame 120. As a result, member 128 is able to flex relative to frame 120, in and out of the plane defined by frame 120.

Plate 110 is preferably integrally connected to a drive tongue 132 that extends along a curvilinear arc that matches the curve of means 160 and path 112. The outside edge of tongue 132 has a raised ridge 134 provided with means, such as slots 136, to cooperate with a sensor. The inside edge 138 of tongue 132 comprises a raised ridge that is provided with a rack 139. Rack 139 is driven by gear 142 of drive means 140, FIG. 2.

Figure 7:
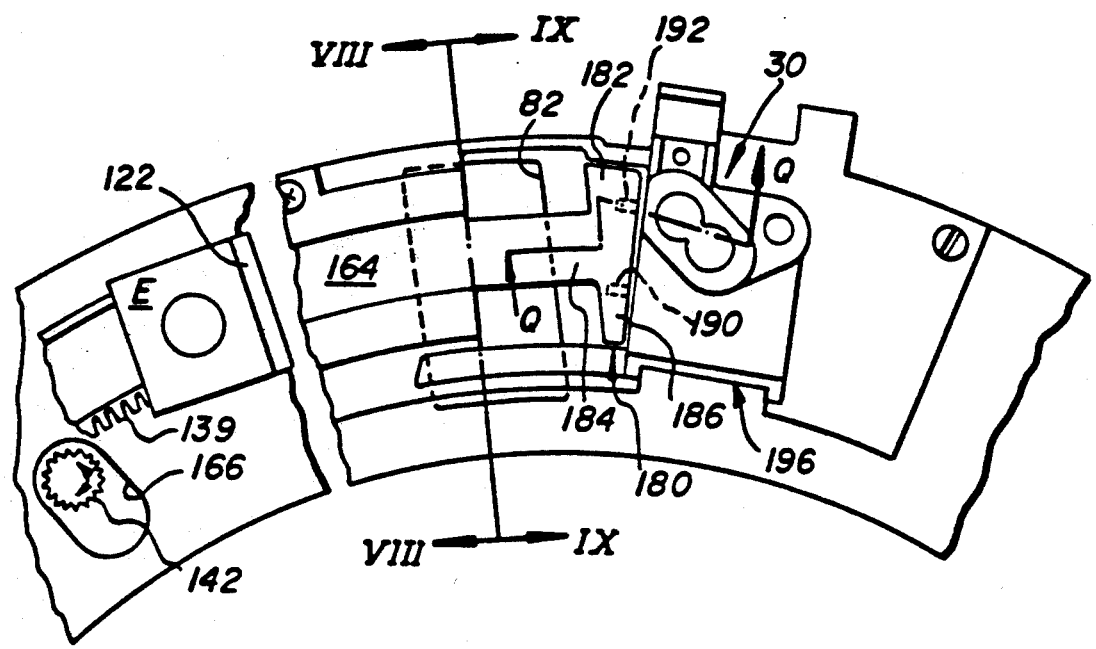
FIG. 7 is a fragmentary plan view of the shuttle apparatus of FIG. 3.
Figure 8:
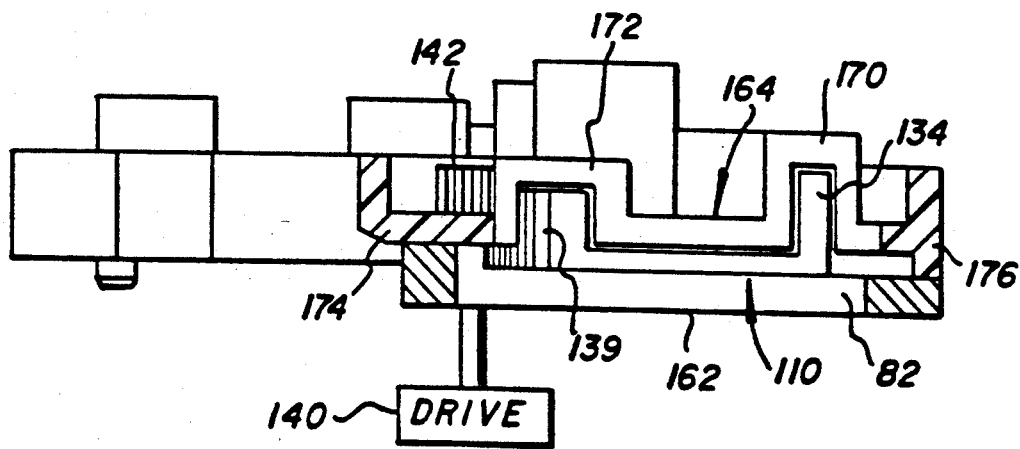
FIGS. 8 and 9 are section views taken generally along the lines VIII—VIII and IX—IX of FIG. 7, respectively.
Figure 9:
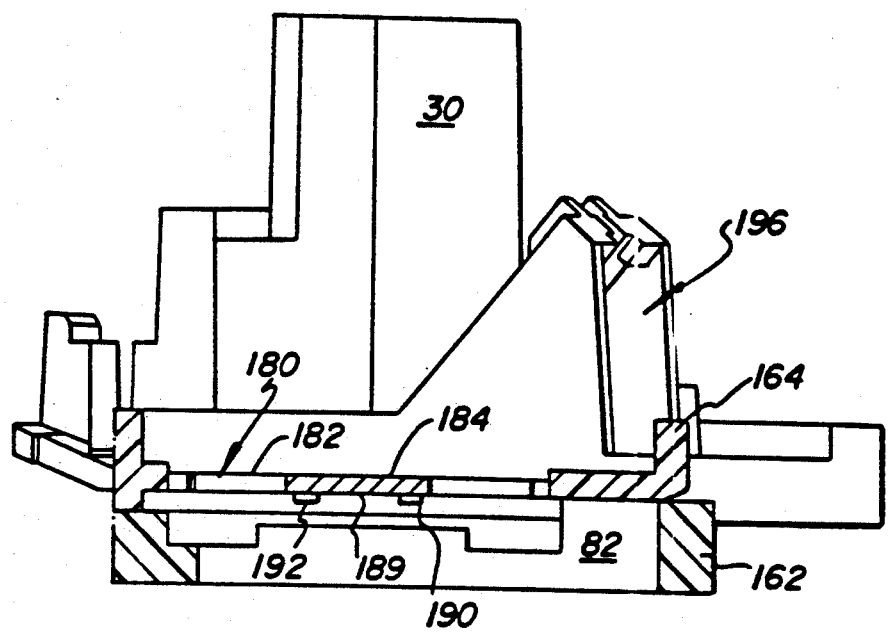

Support means 160 for plate 110 and its tongue 132 comprises two opposed track members 162 and 164, FIGS. 7-9, between which plate 110 and tongue 132 reciprocate. Members 162 and 164 preferably have the same arcuate curvature as tongue 132. Most preferably, member 162 is generally flat, FIG. 8, and is apertured at 82 for element discharge, and at 166 to receive drive gear 142, FIG. 7. Opposed track member 164 is railshaped at 170, 172 to accommodate ridge 134, and rack 139 of tongue 132, FIG. 8. Member 164 is secured to lower member 162 at bottom portions 174 and 176. Member 164 is apertured to accommodate gear 142, and further at 74, FIGS. 1 and 2, to provide for wash station 70.

Figure 12:
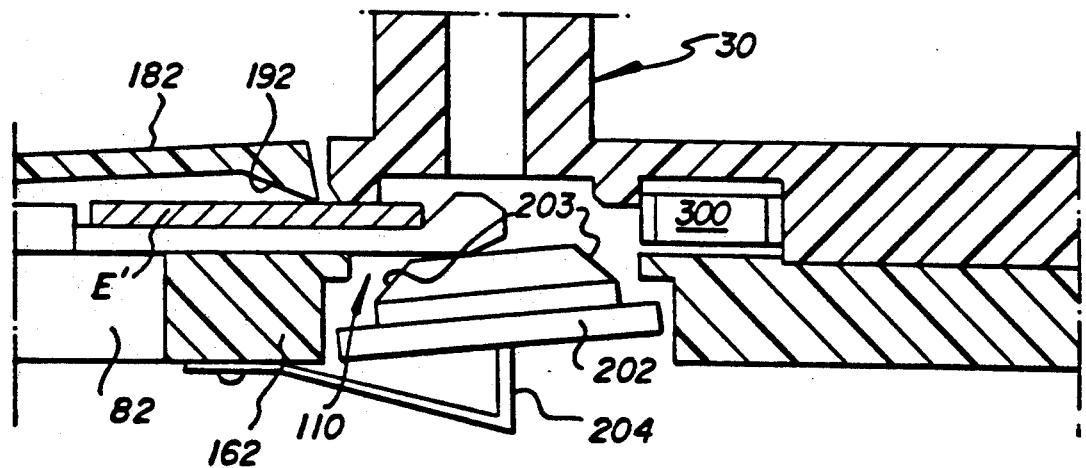

In another aspect of the invention, there is provided stop means 180 that allow a washed test element to be returned and retained at station 30, FIG. 7. For this purpose, stop means 180 is disposed adjacent the injection path 29,32, at the intersection location of that path with path 112. Most preferably, stop means 180 comprise a flexure plate 182, FIGS. 2 and 7, that is cantilevered by arm 184 from the rest of upper member 164. The outer edge 186 of plate 182 provides a shoulder against which a test element abuts, when it moves along path 29,32. In addition, flexure plate 182 includes on its undersurface 189, FIG. 9, one and preferably two camming feet 190, 192, FIGS. 7 and 9, which allow plate 182 to ride up over a test element, FIG. 12, being moved by plate 110 on path 112 to path 29, 32.

Optionally, a viewing port 196 can be provided, FIG. 4, adjacent station 30, to allow a wetness detector to scan a slide element as liquid is dispensed thereon.

Figure 3:
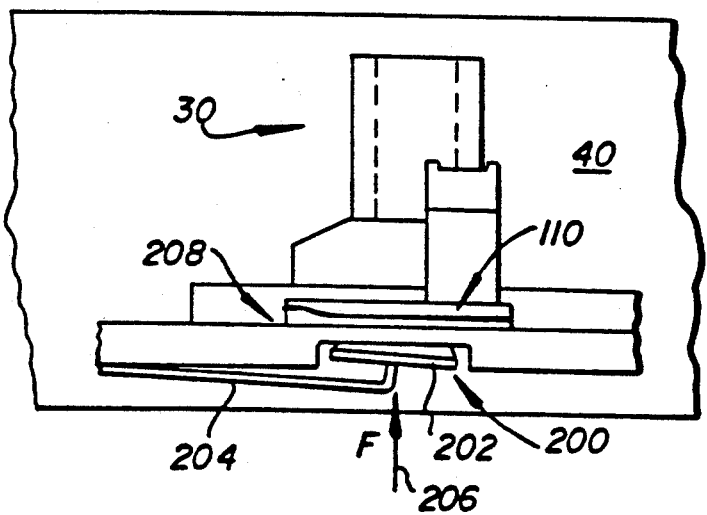
FIG. 3 is a fragmentary side elevational view taken generally along the line III—III of FIG. 1.
Figure 11:
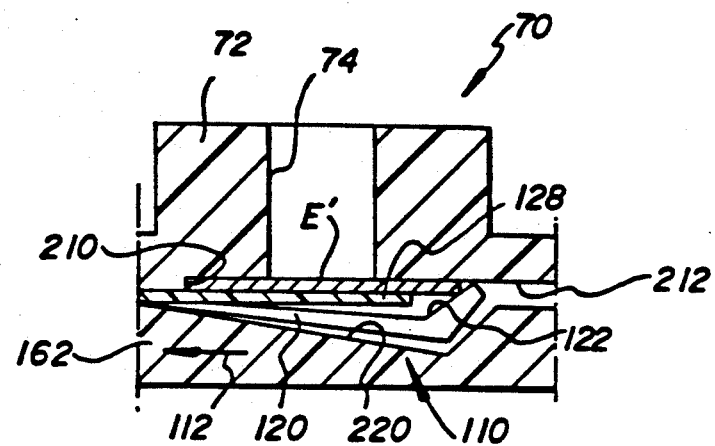

The apparatus of the invention further includes bias means 200 at station 30, FIG. 3, and locating surfaces 210, 212, FIG. 11, at wash station 70. In station 30, the bias means 200 acts to bias a test element up against the tip locator 34 at station 30. Means 200 comprise a platen 202 that is beveled at 203, FIG. 12, and a spring 204 exerting an upward force F, arrow 206, FIG. 3. Entrance slot 208 allows a test element to be inserted into station 30 and onto either platen 202 or shuttle plate 110, as shown in FIG. 3.

At station 70, FIG. 11, stop surface 210 is provided to stop the movement of a test element E' even as plate 110 continues to advance slightly further, arrow 112. Undersurface 212 at station 70 is the ceiling against which element E' is pushed by flexible support member 128. An opposite depression 220 is formed in lower track member 162 to receive frame 120 of plate 110, that is cammed downwardly due to camming surface 122 of frame 120 pressing against element E'. In addition, a camming surface, not shown, extending diagonally from surface 210 ensures proper location of element E' in the direction out of the plane of FIG. 11.

Figure 10:
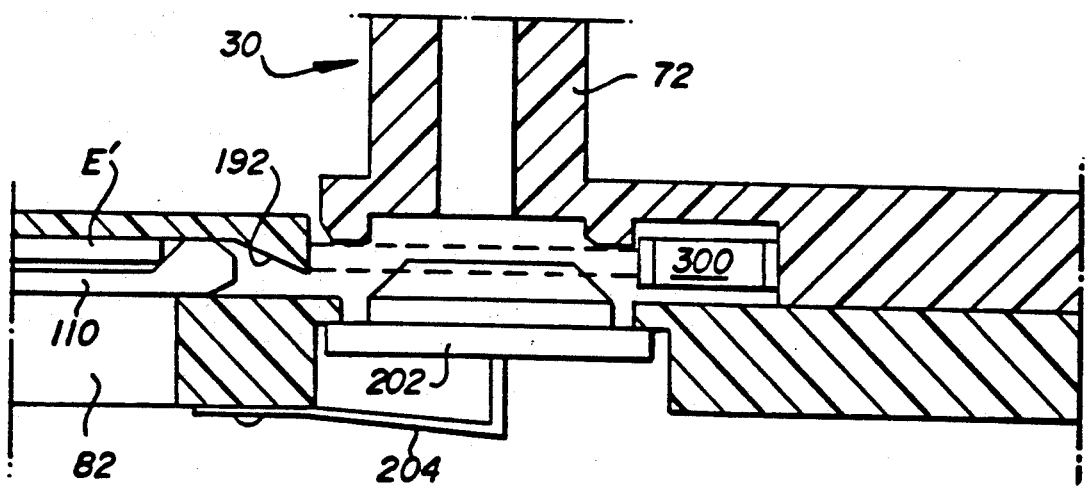
FIGS. 10, 11, 12 and 13A-13C are fragmentary section views taken generally along the line Q—Q of FIG. 7, illustrating the sequential operation of the shuttle apparatus.

The wash method will be readily apparent from the previous description. In brief, plate 110 is moved by drive means 140 into position so as to intercept an ejected test element E', FIG. 10, thus preventing element E' from falling out discharge aperture 82.

Next, plate 110 moves along path 112 due to the action of drive means 140, until element E' is at wash station 70, FIG. 11. A suitable pipette, not shown, is inserted into aperture 74, and boss 72 serves to hold the pipette the proper distance within station 70. At the same time, plate 110 pulls element E' up against stop shoulder 210 and the flexure of support member 128 is such as to push element E' up against undersurface 212 of station 70. The proper spacing of the pipette and element E' is now defined, which can be, e.g., about 1.3 mm. About 10 μL of wash liquid is preferably ejected onto the element E', preferably at a rate of about 0.5 μL per second, for 20 seconds. However, other rates can also be used, depending on the hydrophilicity of the element being washed.

After washing, plate 110 is now returned towards station 30 and away from station 70, by reversing the direction of rotation of gear 142.

In accord with another aspect of the invention, the wash method differs from that previously used in that the washed element is returned to the station from which elements that have just received sample are loaded into the incubator. This allows the analyzer to be simplified in that the same pusher blade used to initially load the element into the analyzer, is reused to re-load the element. More specifically, as plate 110 and element E' move from the vicinity of discharge path 82 into station 30 where path 112 intersects path 29,32, FIG. 12, camming surfaces 190 and 192 allow stop means flexure plate 182 to ride up over element E'. At the same time, platen 202 is cammed downwardly, due to the camming action caused by surface 203.

Figure 13A:
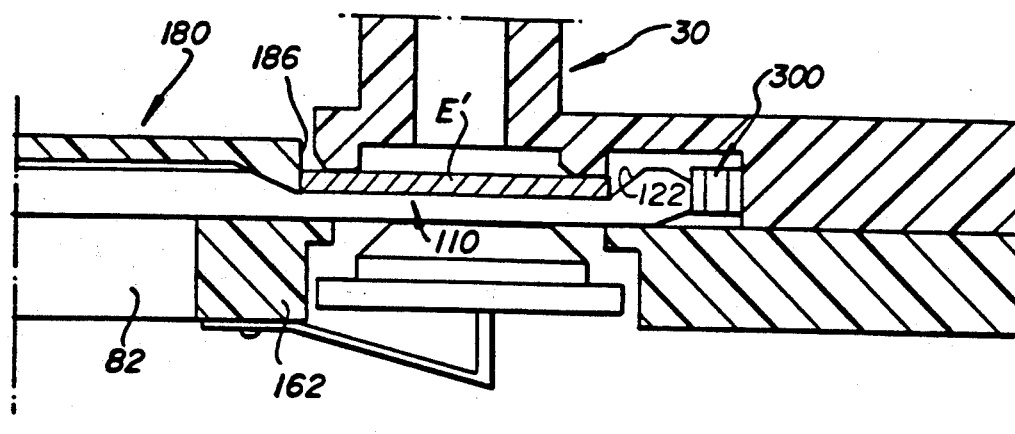
Figure 13B:
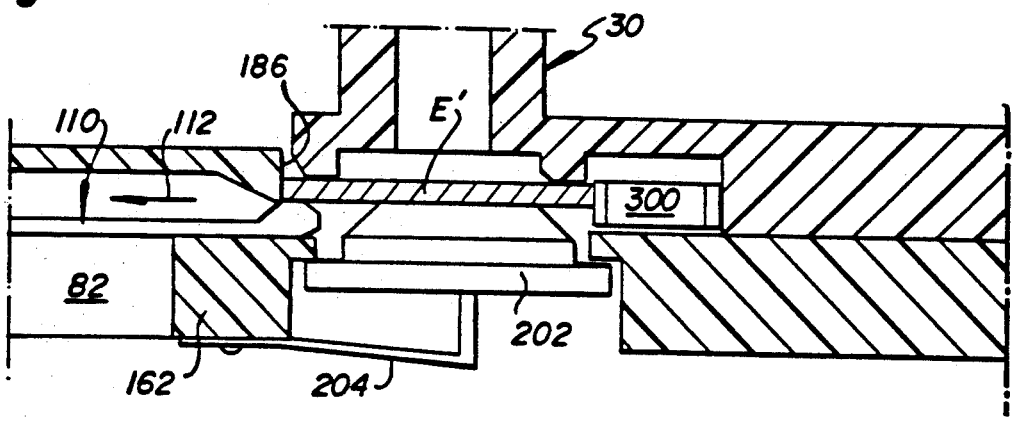
Figure 13C:
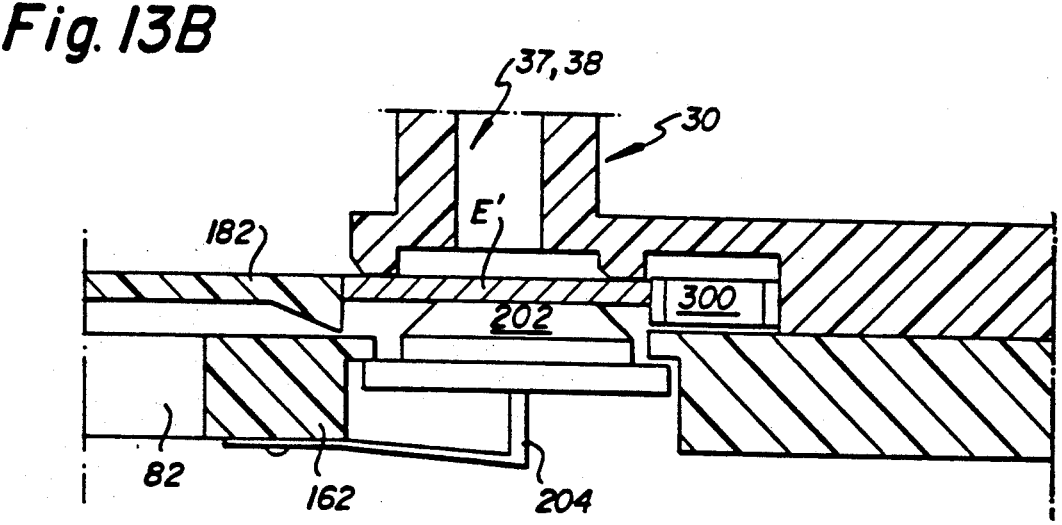

Once element E' is returned to station 30, FIGS. 13A-13C, stop means 180 is effective to restrain element E' from leaving station 30 with plate 110. That is, shoulder 186 slips behind element E', FIG. 13A, and cam surface 193 allows plate 110 to slip under element E', so that as plate 110 starts moving out of station 30 along the path of arrow 112, FIG. 13B, shoulder 186 holds element E' from following plate 110. Plate 110 is carefully advanced into the position shown in FIG. 13A, by drive means 140, to ensure element E' is advanced past shoulder 186. The steps of travel of means 140 can be adjusted to ensure that this advance occurs. Meanwhile, platen 202 is pushed up by its spring 204, to further hold element E'. That is, plate 110 pushes element E' up due to the upward force of the platen. When plate 110 is completely withdrawn, FIG. 13C, element E' is positioned for reloading into incubator 40, using pusher blade 22. (The positioning of the parts in FIG. 13C is also their position when an element is first loaded into station 30 for dispensing patient sample and/or reference liquid via apertures 36, 37 and 38, of which 38 is not shown.)

A bumper spring 300 is preferably included, FIG. 13A, against which plate 110 pushes when element E' is being returned to station 30. This spring prevents overtravel of plate 110, but primarily it assists in holding test elements against stop shoulder 186, FIG. 13B.

Following reloading of the washed slide into the incubator, which occurs after the events illustrated in FIG. 13C, further incubation and a reading of the element occur. When a read element is ready for disposal, ejection occurs using pusher blade 48, arrow 310, FIG. 2, except this time, plate 110 is not in position at station 80 to catch the element. Instead, it falls through aperture 82, FIG. 1, into a suitable disposal container.

The invention has been described in detail with particular reference to preferred embodiments thereof, but it will be understood that variations and modifications can be effected within the spirit and scope of the invention.

What is claimed is:

1. In an analyzer comprising at least one processing station including an incubator, means for injecting a test element bearing a sample liquid along a first path into one of said processing stations, means for ejecting a test element from said one station, and discharge means defining a second path for carrying an ejected test element away from said one station, the improvement wherein said analyzer further includes a stop mechanism between said first path and said second path, said mechanism including a) a stop shoulder adjacent said first path to prevent a test element on said first path from moving off said first path towards said second path, and b) a camming surface under and adjacent to said stop shoulder, said camming surface being shaped to cause said stop mechanism to ride up over a test element moved from a portion of said second path to said first path, so that a test element can be moved from said portion of second path to said first path, but not from said first path to said portion of second path.

2. An analyzer as defined in claim 1, wherein said one processing station comprises said incubator.

3. An analyzer as defined in claim 1 or 2, and further including a wash station, track-defining means extending from said second path to said wash station and then to said first path, and moving means for moving a test element along said track-defining means.

4. An analyzer as defined in claim 3, wherein said moving means comprise a frame having opposed, raised shoulders dimensioned to retain a test element between said shoulders to prevent a held element from being undesirably displaced off said moving means.

5. An analyzer as defined in claim 4, and further including in said moving means a central support member disposed between said shoulders, said member being flexibly connected to said frame to allow relative flexing between said support member and said frame in and out of the plane of said frame.

6. An analyzer as defined in claim 5, wherein said support member is cantilevered from said frame at only one side thereof, so as to be capable of flexing in and out of the plane of said frame.

7. An analyzer as defined in claim 5, wherein said shoulders are disposed on the leading and trailing edges, respectively, of said moving means as it moves along said track-defining means from said wash station, said leading edge shoulder being provided with a shoulder cam surface sloped sufficiently to allow said support member to ride under a test element that is on said support member when said test element is held from movement along said track-defining means by said stop mechanism.

* * * * *